US006280855B1

(12) United States Patent
Viikari et al.

(10) Patent No.: US 6,280,855 B1
(45) Date of Patent: Aug. 28, 2001

(54) INTERMEDIATE PRODUCT FOR PREPARATION OF LIGNIN POLYMERS AND USE THEREOF FOR PRODUCTION OF WOOD MATERIALS

(75) Inventors: Liisa Viikari, Helsinki; Anneli Hase, Espoo; Pia Qvintus-Leino, Espoo; Marja-Leena Niku-Paavola, Espoo, all of (FI)

(73) Assignee: Neste Chemicals Oy, Espoo (FI)

( * ) Notice: Subject to any disclaimer, the term of this patent is extended or adjusted under 35 U.S.C. 154(b) by 0 days.

(21) Appl. No.: 09/341,578

(22) PCT Filed: Jan. 14, 1998

(86) PCT No.: PCT/FI98/00021

§ 371 Date: Oct. 25, 1999

§ 102(e) Date: Oct. 25, 1999

(87) PCT Pub. No.: WO98/31825

PCT Pub. Date: Jul. 23, 1998

(30) Foreign Application Priority Data

Jan. 14, 1997 (DE) .............................. 197 00 907

(51) Int. Cl.⁷ ............................ B32B 21/06; C08G 63/00
(52) U.S. Cl. ....................... 428/535; 527/400; 527/403; 435/101; 524/73; 524/74
(58) Field of Search .................... 527/400, 403; 435/101; 524/73, 74; 428/535

(56) References Cited

U.S. PATENT DOCUMENTS

| 4,432,921 | * | 2/1984 | Haars et al. | 264/109 |
| 5,846,788 | * | 12/1998 | Pedersen et al. | 439/101 |
| 6,072,015 | * | 6/2000 | Bolle et al. | 527/400 |
| 6,187,136 | * | 2/2000 | Pedersen et al. | 162/65 |

FOREIGN PATENT DOCUMENTS

WO 95/08588 A1  3/1995 (WO).
WO 95/23232 A1  8/1995 (WO).

* cited by examiner

*Primary Examiner*—Samuel A. Acquah
(74) *Attorney, Agent, or Firm*—Birch, Stewart, Kolasch & Birch, LLP

(57) ABSTRACT

The invention relates to an intermediate product for the preparation of polymerizates from lignin derivatives obtained from the cellulose industry. The intermediate product is produced by treating the lignin derivatives with enzymes capable of oxidizing phenol in the presence of oxidizing agents. According to the invention the lignin derivatives are subjected to the enzymatic treatment for more than 3 hours in the presence of air, or they are subjected to an enzymatic treatment for more than 10 min, whereby air or oxygen is introduced. The lignin polymers obtained from the polymerization of lignin derivatives performed in the presence of active intermediate products are suited for use in the production of binding agents for wood materials.

8 Claims, 1 Drawing Sheet

Beginning of field: 2954.70 gauss
Microwave: 9.56 GHz
ESR attenuation: 20.00 dB
Mod. frequency: 100.00 MHz End of field: 3754.10 gauss
Working point: 3300.00 gauss
Temperature: 77.00 K
Mod. amplitude: 4.00 gauss

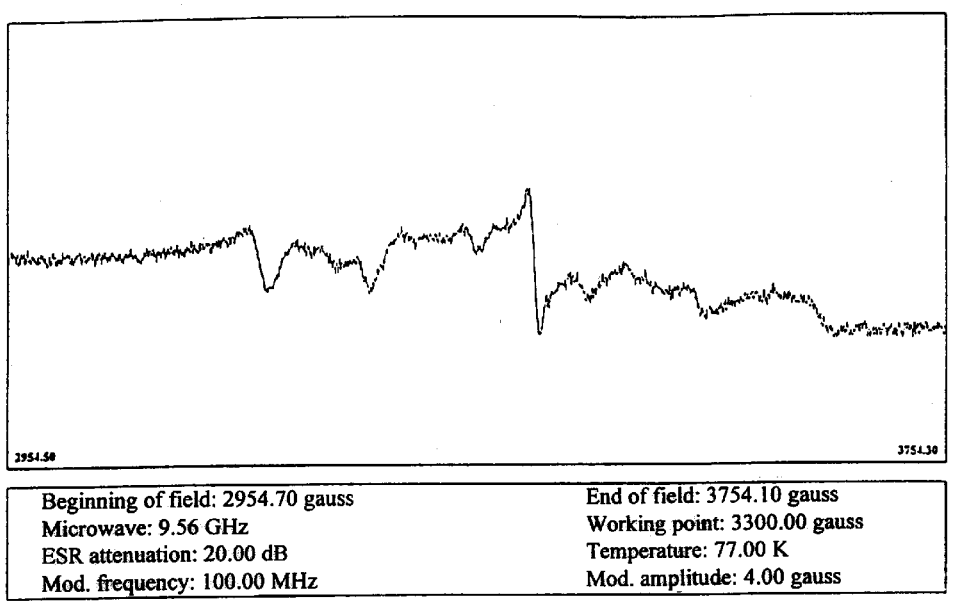
Fig. 1: The ESR spectrum of BSM with a 1 % lignin sulphonate addition with added laccase (4U/ml); 9.5 GHz, 20 dB, modulation 4 and 8 g.
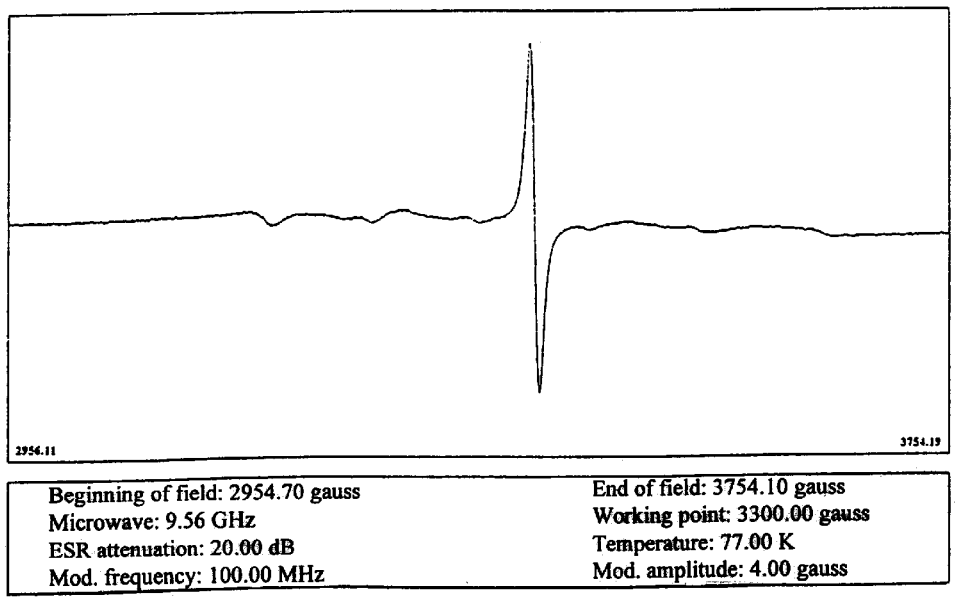
Fig. 2: The ESR spectrum of a culture filtrate of cultures of the strain of fungi *Pleurotus ostreatus* F6 (culture medium: BSM containing an addition of lignin sulphonate) after 32 days of incubation, with a laccase addition (4U/ml); 9.5 GHz, 20 dB, modulation 4 and 8 g.

INTERMEDIATE PRODUCT FOR PREPARATION OF LIGNIN POLYMERS AND USE THEREOF FOR PRODUCTION OF WOOD MATERIALS

This application is the national phase under 35 U.S.C. § 371 of PCT International Application No. PCT/FI98/00021 which has an International filing date of Jan. 14, 1998, which designated the United States of America.

The present invention relates to an intermediate product for the preparation of polymerizates from lignin derivatives formed during pulping as well as to the use of said intermediate products in the production of wood materials.

In DE 37 992 C2, a process is described for the preparation of a binding agent for woodbased materials using phenolic substances, particularly lignin sulphonate, wherein enzymes are added to the phenolic substance for the purpose of activation, the enzymes polymerizing phenols oxidatively by a radical mechanism whereby the phenolic substance becomes an active binding agent. It is, indeed, previously known that this reaction takes place in the presence of oxygen, e.g. the oxygen in air, but such an activated binding agent has not been implemented previously for a longer period of time or by intensive aeration with oxygen.

It was unexpectedly found that lignin derivatives from the cellulose industry, such as kraft lignin or lignin sulphonate, when reacted intensively with oxygen, air, or other chemical oxidizing agent, or when the reaction is of long duration, form as an intermediate product a lignin product particularly capable of reacting. This intermediate product can be isolated and stored for longer periods, and it reacts with further, unactivated lignin derivatives to form a macromolecular polymerizate. The intermediate product can be characterized by reacting the material with laccase. After this reaction it has a typical ESR spectrum with a phenoxy radical signal in the region of about 3400 gauss, which signal, however, being a typical radical signal, does not remain unchanged in the long run. Unexpectedly, however, the higher reactivity of the intermediate product remains constant even after longer periods, such as months. Thus, this activated intermediate product is significantly more active when reacting with phenol-oxidizing enzymes than unpretreated lignin derivatives wherefore it forms the typical ESR spectrum with essentially greater intensity than lignin derivatives which have not been pretreated in this manner.

The intensity of the signal of the activated intermediate product is at least more than five times that of the signal of the lignin derivative serving as feedstock. The signal is measured, for instance, under the following conditions: 77° C.; 9.5 GHz, ESR attenuation 20 dB, mod. freq. 100 MHz; mod. amplitude 4.0 gauss.

The activated intermediate product can be obtained by treating technical lignin, such as lignin sulphonate, kraft lignin, organosolvlignin, acetosolvlignin or ASAM lignin, which are obtained from cellulose production, for a fairly long time in the presence of enzymes capable of oxidizing phenolic groups with air or oxygen. Already after a period of about three hours, particularly, however, after twenty hours, an increase in the phenoxy radical signal can be observed. When air or oxygen under pressure is introduced, the increased signal will appear after a considerably shorter period of time, for instance after 30 min.

The intermediate product can also be obtained by means of chemical oxidizing agents. For this purpose, agents common in lignin chemistry, such as potassium permanganate, bichromates or ozone may be used.

The enzymatic formation of the activated intermediate product is only possible in the presence of greater amounts of oxygen. Because only 9 mg/l of oxygen is dissolved in water in room temperature, the formation of the intermediate product is only enhanced by an increased supply of oxygen, either by aeration or by adding oxidizing agents.

Even when the oxygen balance is set for a longer period of time, a sufficient amount of oxygen may after a while have affected the lignin derivative.

In this connection it has emerged that such an amount of oxygen should be incorporated in the lignin-containing system that an essentially complete oxidation of the lignin is attained under the reaction conditions used. This need for oxygen, depending on the lignin used, was calculated as being 0.5 to 20 mg $O_2$/g lignin, preferably 1 to 10 mg. In principle, however, it is of advantage to use excess oxygen.

The activated intermediate product will react in the presence of enzymes which oxidize phenolic groups for instance with unactivated lignin derivatives such as are obtained from, e.g. cellulose production, when polymeric lignin products are being formed, whereby the molar masses obtained are essentially higher than those obtained when enzymes capable of oxidizing phenols are allowed to affect lignin derivatives without the presence of activated lignin derivatives.

They are usually at least twice as high.

The lignin polymers obtained by polymerizing lignin derivatives in the presence of active intermediate products are suited for use when highly active binding agents for wood materials are produced.

BRIEF DESCRIPTION OF THE DRAWINGS

In comparison to the lignin used as base material the activated lignin has an ESR spectrum having an essentially increased intensity of the phenoxyradical signal. This is shown in FIGS. 1 and 2. In FIG. 1, the ESR spectrum of a 1% lignin sulphonate is shown to which laccase (4 U/ml) has been added, after an incubation time of 30 min without any oxygen treatment. In FIG. 2 the corresponding spectrum is shown for lignin sulphonate which has been incubated with laccase for 20 hours under an increased oxygen supply whereafter it has been treated in an autoclave and stored for three months. After renewed incubation with laccase (4 U/ml, 30 min, incubation without oxygen treatment) a comparison of the strongest signal at about 3400 gauss with the background signals will show that, in relation to FIG. 1 the intensity of the phenoxyradical signal was increased to at least five times the original level.

The invention is explained in more detail in the following with the help of a number of working examples:

EXAMPLE 1

20 g of lignin sulphonate is dissolved in 80 ml of McIlvaine buffer solution, pH 5.5, and mixed with 800 U/ml of laccase. The solution is shaken in a 500 ml Erlenmeyer flask in a water bath at 37° C. for 20 h. Next, the solution is treated in an autoclave. The obtained lignin sulphonate is stored for two months. After a renewed incubation with laccase (4 U/ml, 30 min, incubation without any oxygen treatment) it has the ESR spectrum of FIG. 2.

EXAMPLE 2

Activated lignin sulphonate in accordance with Example 1 is mixed with kraft lignin at a mixing ratio of 1:10, the concentration being 100 mg/1 ml suspended in buffer solution, whereafter it is incubated in a sealed test glass with laccase (500 U/ml) without any particular oxygen treatment for 6 hours. Simultaneously, corresponding reference tests were run with unactivated lignin and incubation without laccase. Next, the lignins were isolated and the molar mass distribution was measured in HPLC.

Thereby the following molar masses were obtained:

| | |
|---|---|
| unactivated kraft lignin | 5,400 g/mol |
| unactivated kraft lignin, incubated with laccase | 6,300 g/mol |
| unactivated kraft lignin and activated lignin without laccase | 6,000 g/mol |
| unactivated kraft lignin and activated lignin incubated with laccase | 11,000 g/mol |

EXAMPLE 3

A 30 % suspension of kraft lignin is mixed with 800 U/ml laccase in a buffer having a pH of 5.5 and shaken intensively at an excess pressure of 2 bar with a quintuple volume of oxygen. After 40 min the solution is isolated.

The solution is admixed with regular mid-layer chips such that the content of lignin is 10% in relation to the chips. This mixture is subjected to pressing by the conventional method at 190° C. at a compression load of 30 kg/cm$^2$ for 11 minutes.

The chip boards thus produced have a transversal tensile strength of 11 MPa. The transversal tensile strength of boards manufactured under similar conditions where kraft lignin and laccase had been used as binding agents without any previous enzymatic activation was 6 MPa.

EXAMPLE 4

Example 3 was repeated such that instead of wood chips wood fibres were admixed with a content of lignin of 10%.

Fibre boards manufactured in a corresponding manner had the following specifications:

| Binding agent | Compression time s/mm | Thickness mm | Swelling 2 h % | Swelling 24 h % | Density kg/m$^3$ | Strength MPa |
|---|---|---|---|---|---|---|
| Activ. lignin | 60 | 10.8 | 3.6 | 6.4 | 813 | 0.52 ± 0.06 |
| UF resin | 13 | 10.7 | 5.9 | 11.2 | 795 | 0.70 ± 0.05 |

What is claimed is:

1. An intermediate product for the production of polymerizates from lignin derivatives obtained from the cellulose industry, the intermediate product being produced by a process which comprises treating the lignin derivatives with enzymes that oxidize phenols in the presence of oxidizing agents, wherein the lignin derivatives
   a) are subjected to the enzymatic treatment for more than 3 hours in the presence of air, or
   b) are subjected to the enzymatic treatment for more than 10 min during which time air or oxygen is introduced, or
   c) are oxidized by a treatment performed with chemical oxidizing agents.
2. The intermediate product of claim 1, wherein the lignin derivatives comprise kraft lignin or lignin sulphonate.
3. The intermediate product of claim 1, wherein the enzymes that oxidize phenols comprise phenol oxidase or laccase.
4. The intermediate product of claim 1, wherein the enzymatic treatment according to step a) is continued for more than 15 hours.
5. The intermediate product of claim 1, wherein the enzymatic treatment according to step b) is continued for more than 30 min.
6. The intermediate product of claim 1, wherein compressed air or pressurized oxygen is introduced to the enzymatic treatment of step b).
7. A method for the preparation of polymerizates from lignin derivatives obtained from the cellulose industry comprising reacting the intermediate product of any one of claims 1 to 6 to form a macromolecular polymerizate.
8. The method according to claim 7 for the preparation of binding agents for wood materials.

* * * * *